US009839747B2

(12) United States Patent
Smith et al.

(10) Patent No.: US 9,839,747 B2
(45) Date of Patent: Dec. 12, 2017

(54) INFUSION PUMPS AND INSERTERS FOR USE WITH SAME

(71) Applicant: perQflo, LLC, Valencia, CA (US)

(72) Inventors: Roger E. Smith, Ivins, UT (US); Scott R. Gibson, Granada Hills, CA (US)

(73) Assignee: perQflo, LLC, Valencia, CA (US)

( * ) Notice: Subject to any disclaimer, the term of this patent is extended or adjusted under 35 U.S.C. 154(b) by 65 days.

(21) Appl. No.: 14/819,721

(22) Filed: Aug. 6, 2015

(65) Prior Publication Data

US 2016/0121045 A1 May 5, 2016

Related U.S. Application Data

(63) Continuation of application No. 13/475,843, filed on May 18, 2012, now Pat. No. 9,114,208.

(60) Provisional application No. 61/487,705, filed on May 18, 2011.

(51) Int. Cl.
| | |
|---|---|
| *A61M 5/158* | (2006.01) |
| *A61M 5/142* | (2006.01) |
| *A61M 5/14* | (2006.01) |
| *A61M 5/168* | (2006.01) |

(52) U.S. Cl.
CPC ............ *A61M 5/158* (2013.01); *A61M 5/142* (2013.01); *A61M 5/1413* (2013.01); *A61M 5/14244* (2013.01); *A61M 5/14248* (2013.01); *A61M 2005/14252* (2013.01); *A61M 2005/14268* (2013.01); *A61M 2005/1581* (2013.01); *A61M 2005/1585* (2013.01); *A61M 2005/16863* (2013.01); *A61M 2205/8256* (2013.01); *A61M 2209/01* (2013.01); *Y10T 29/49826* (2015.01)

(58) Field of Classification Search
CPC .............. A61M 5/158; A61M 5/14248; A61M 5/1413; A61M 2005/14252; A61M 2005/1585
See application file for complete search history.

(56) References Cited

U.S. PATENT DOCUMENTS

| | | |
|---|---|---|
| 5,176,662 A | 1/1993 | Bartholomew |
| 5,257,980 A | 11/1993 | Van Antwerp et al. |
| 5,584,813 A | 12/1996 | Livingston et al. |
| 5,779,665 A | 7/1998 | Mastrototaro et al. |
| 5,851,197 A | 12/1998 | Marano et al. |
| 5,951,521 A | 9/1999 | Mastrototaro et al. |
| 6,056,718 A | 5/2000 | Funderburk et al. |
| 6,093,172 A | 7/2000 | Funderburk et al. |
| 6,254,586 B1 | 7/2001 | Mann et al. |
| 6,293,925 B1 | 9/2001 | Safabash et al. |
| 6,461,331 B1 | 10/2002 | Van Antwerp |
| 6,520,938 B1 | 2/2003 | Funderburk et al. |
| 6,607,509 B2 | 8/2003 | Bobroff et al. |
| 6,902,207 B2 | 6/2005 | Lickliter |
| 6,997,907 B2 | 2/2006 | Safabash et al. |
| 7,207,974 B2 | 4/2007 | Safabash et al. |
| 7,303,543 B1 | 12/2007 | Maule et al. |
| 7,318,816 B2 | 1/2008 | Bobroff et al. |
| 7,329,239 B2 | 2/2008 | Safabash et al. |

(Continued)

*Primary Examiner* — Bradley Osinski
(74) *Attorney, Agent, or Firm* — Henricks, Slavin & Holmes LLP

(57) ABSTRACT

Ambulatory infusion pumps, pump assemblies, and disposable assemblies, including cartridges, baseplates, cannulas, inserters, and related components therefor, as well as component combinations and related methods.

20 Claims, 13 Drawing Sheets

(56) References Cited

U.S. PATENT DOCUMENTS

| | | |
|---|---|---|
| 7,455,663 B2 | 11/2008 | Bikovsky |
| 8,905,972 B2 | 12/2014 | Smith et al. |
| 9,114,208 B2 | 8/2015 | Smith et al. |
| 2008/0319416 A1 | 12/2008 | Yodfat et al. |
| 2009/0198215 A1 | 8/2009 | Chong et al. |
| 2010/0217105 A1* | 8/2010 | Yodfat ............... A61B 5/14503 600/365 |

* cited by examiner

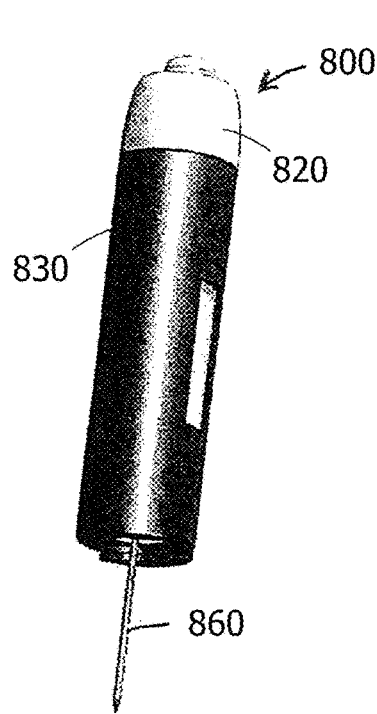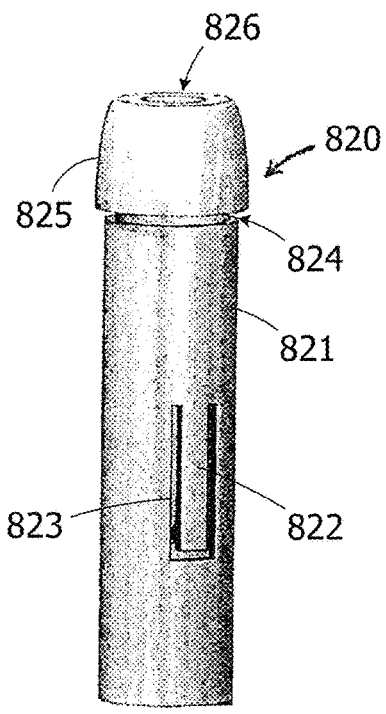
FIG. 5     FIG. 5A
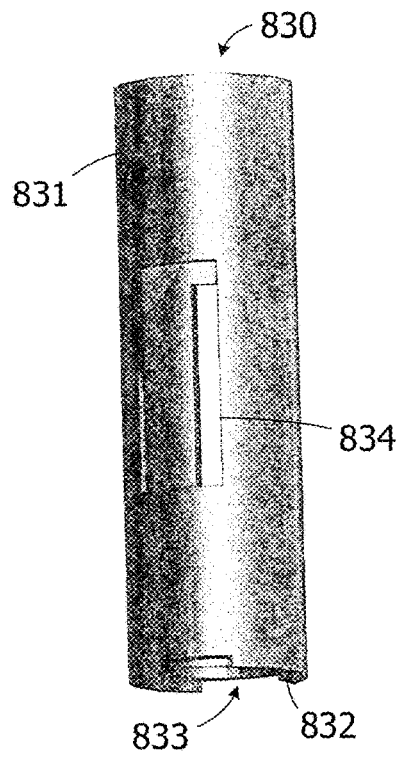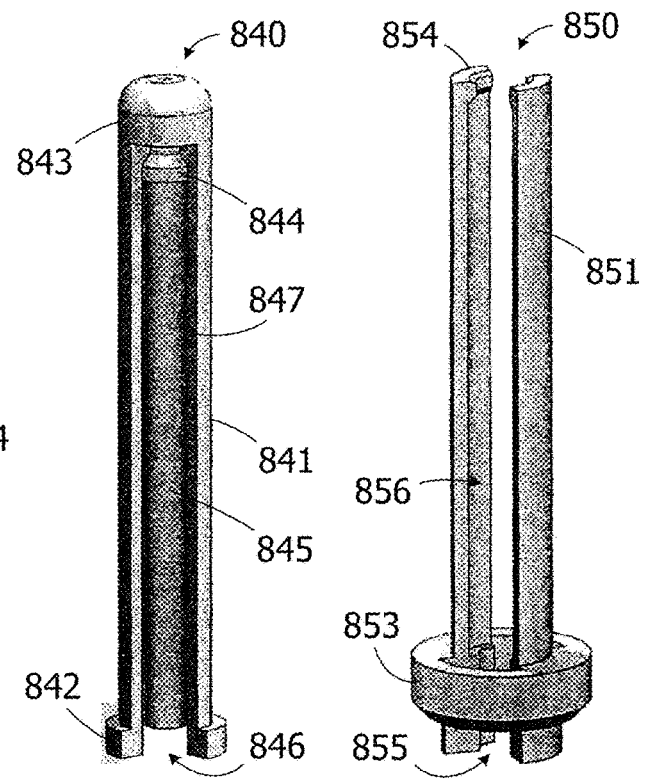
FIG. 5B     FIG. 5C     FIG. 5D

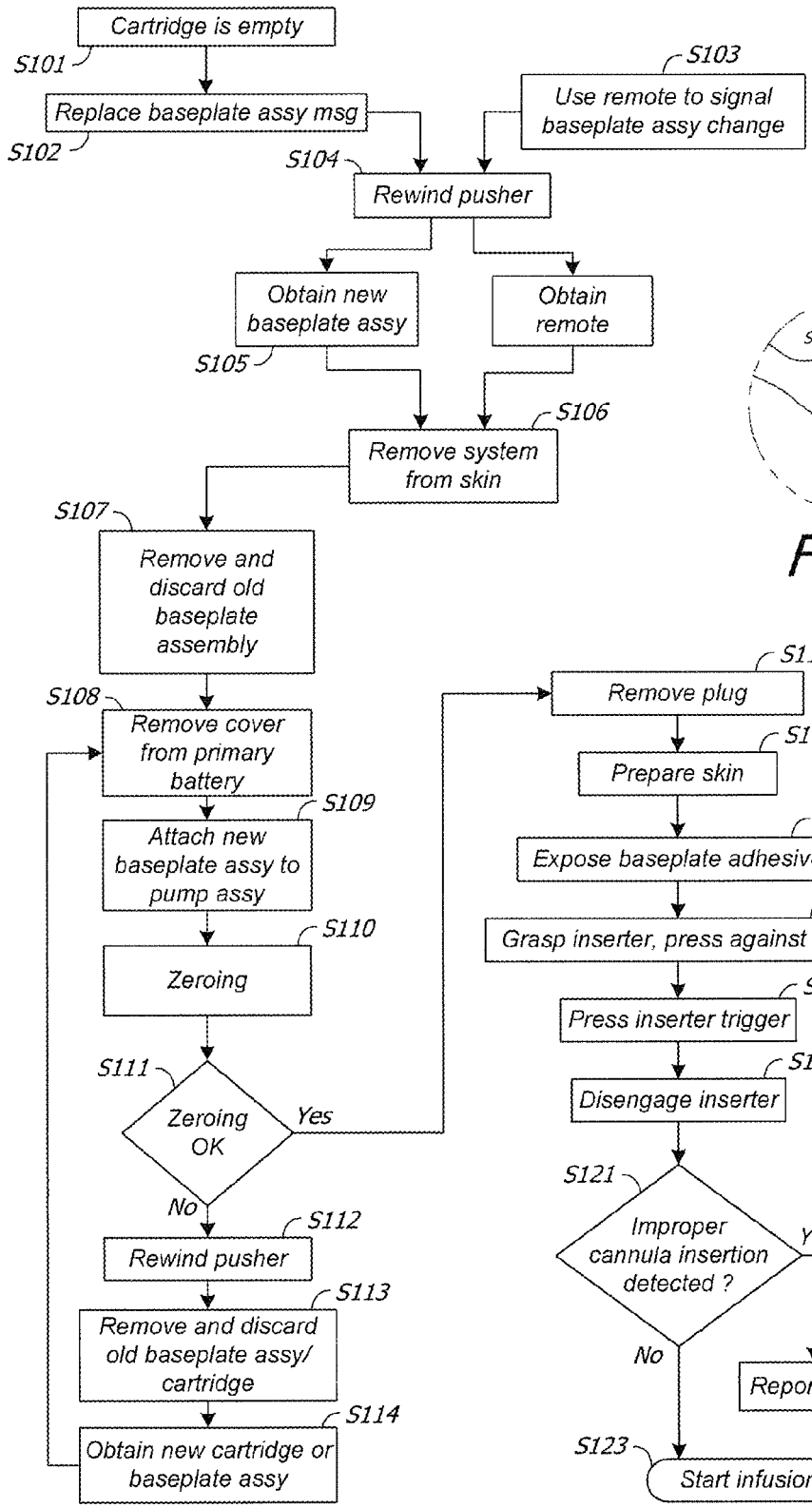
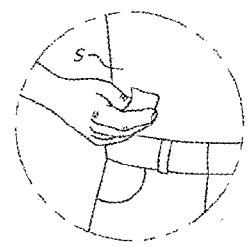
FIG. 9
FIG. 8

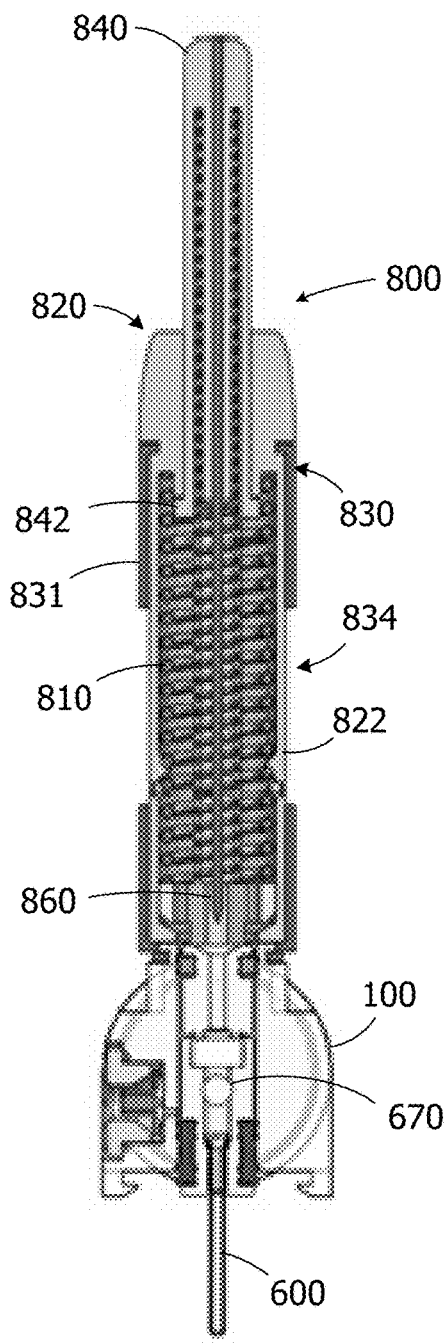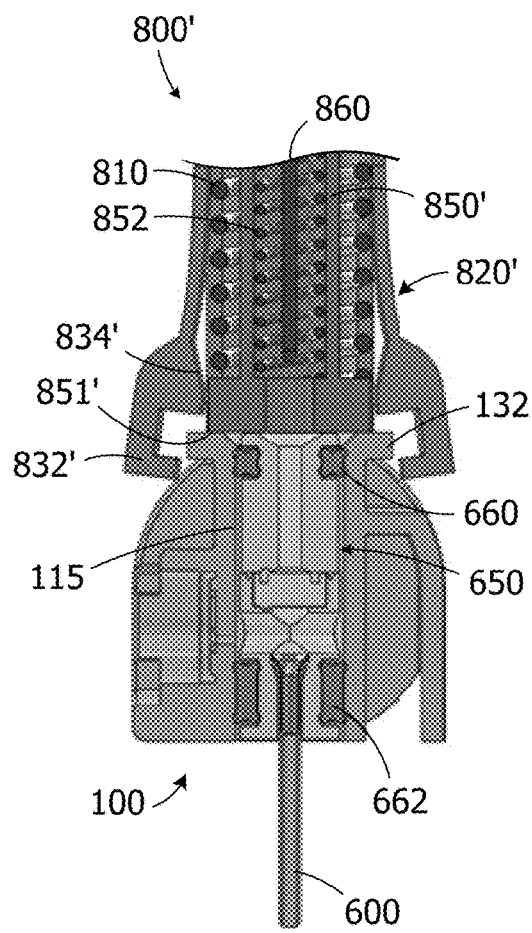
FIG. 10B
FIG. 11

INFUSION PUMPS AND INSERTERS FOR USE WITH SAME

CROSS-REFERENCE TO RELATED APPLICATIONS

This application is a continuation of U.S. application Ser. No. 13/475,843, filed May 18, 2012, now U.S. Pat. No. 9,114,208, which claims the benefit of U.S. provisional application Ser. No. 61/487,705, filed May 18, 2011 and entitled "Infusion Pumps," which is incorporated herein by reference in its entirety.

This application is related to U.S. application Ser. No. 13/300,574, filed Nov. 19, 2011, now U.S. Pat. No. 8,905,972, which claims the benefit of U.S. provisional patent application Ser. No. 61/415,830, filed Nov. 20, 2010, and entitled "Infusion Pumps," both of which are incorporated herein by reference in their entirety.

BACKGROUND

1. Field

The present devices and methods relate generally to ambulatory infusion pumps and inserters for use with same.

2. Description of the Related Art

Ambulatory infusion pumps (also referred to herein simply as "infusion pumps") are relatively small, at least substantially self-contained devices that are used to introduce drugs and other infusible substances (collectively "medicament") into patients' bodies. Some infusion pumps are configured to be worn on a belt, carried in a clothing pocket, or the like. Other infusion pumps are configured to be adhered to skin in patch-like fashion. Infusion pumps are advantageous in that they may be used to, for example, subcutaneously introduce (or "infuse") medicament on an ongoing or even continuous basis outside of a clinical environment. Infusion pumps are also advantageous in that they greatly reduce the frequency of subcutaneous access events such as needle-based shots. One example of a medicament that may be introduced by an infusion pump is a liquid formulation of insulin. Other exemplary medicaments that may be introduced by an infusion pump include, but are not limited to, drugs that treat cancers and drugs that suppress the perception of pain.

Many conventional infusion pumps have improved patient health and quality of life. Nevertheless, the present inventors have determined that conventional infusion pumps are susceptible to a wide range of improvements. By way of example, but not limitation, the present inventors have determined that it would be desirable to provide an infusion pump that is smaller, more accurate and/or provides more operational flexibility than conventional infusion pumps.

SUMMARY

An inserter in accordance with at least one of the present inventions includes a main body and a trocar assembly movable relative to the main body. The trocar assembly may include a first trocar assembly member, a second trocar assembly member operably connected to the first trocar assembly member, a first force member operably connected to the first and second trocar assembly members, a first lock apparatus having a locked state that prevents movement of the first and second trocar assembly members relative to one another, and a trocar carried by the second trocar assembly member. The inserter may also include a second force member operably connected to the main body and to the trocar assembly, a second lock apparatus having a locked state that prevents movement of the trocar assembly relative to the main body relative, and an actuator carried by the main body and rotatable about the main body from a first position, that prevents the second lock apparatus from being in the unlocked state, to a second position that allows the second lock apparatus to be in the unlocked state.

A method of inserting a cannula in accordance with at least one of the present inventions includes the steps of driving a cannula assembly and a trocar in a first direction with an inserter in response to rotation by a user of an outer portion of the inserter relative to an inner portion of the inserter, and driving the trocar in a second direction, opposite the first direction, to a withdrawn position without additional action by the user and in response to the cannula assembly reaching a fired position.

An assembly in accordance with at least one of the present inventions includes a medicament cartridge including a reservoir, a through-bore and a medicament outlet, an inserter mounted on the medicament cartridge, and a cannula assembly including a support structure defining a trocar lumen and a hole, first and second seals on the support structure on opposite sides of the hole, and a cannula secured to the support structure and in fluid communication with the hole. The cannula assembly is located in a storage position where a portion of the cannula assembly is within the medicament cartridge through-bore and the first seal is aligned with the medicament outlet.

A system in accordance with at least one of the present inventions includes an infusion pump assembly and a disposable assembly. The infusion pump assembly may include a housing and a pump module and rechargeable battery in the housing. The disposable assembly may include a baseplate, a disposable battery and medicament cartridge assembly on the baseplate, and may be configured to be attached to the infusion pump housing. In addition, the disposable assembly may include an inserter for automatically inserting a cannula. Systems and methods related to such cannula insertion and related trocar and inserter removal are described.

The features and attendant advantages of the present inventions will become apparent as the inventions become better understood by reference to the following detailed description when considered in conjunction with the accompanying drawings.

BRIEF DESCRIPTION OF THE DRAWINGS

Detailed description of exemplary embodiments will be made with reference to the accompanying drawings.

FIG. 1A is an exploded perspective view of an exemplary infusion pump system including a pump assembly and a disposable assembly with the inserter in place.

FIG. 5 is a perspective view of an exemplary automatic cannula inserter.

FIGS. 5A-5D are perspective views of individual components of the inserter illustrated in FIG. 5.

FIG. 8 is a flow chart illustrating an exemplary disposable assembly removal and replacement method.

FIG. 9 is a front view showing a patient's skin being cleaned.

FIG. 10B is a section view, offset 90 degrees from the orientation illustrated in FIG. 10A, of the components illustrated in FIG. 10A.

FIG. 11 is a section view illustrating an alternative inserter shown after inserter firing and cannula insertion.

DETAILED DESCRIPTION

The following is a detailed description of the best presently known modes of carrying out the inventions. This description is not to be taken in a limiting sense, but is made merely for the purpose of illustrating the general principles of the inventions.

It should also be noted here that the specification describes structures and methods, mainly in the context of cartridge-based infusion pumps, which are especially well-suited for the subcutaneous delivery of very high concentration insulin (e.g., the U-500 insulin discussed below). Nevertheless, it should be appreciated that the present inventions are applicable to a wide variety of infusion pumps and medicaments. By way of example, but not limitation, many of the present inventions are also applicable to infusion pumps that are not cartridge-based (e.g., pumps with refillable reservoirs and single use pumps). Also, the inventions may employ, for fluid displacement, a cartridge with a plunger, a fluid displacement device in the form of a plunger pusher, and a drive mechanism that includes a motor, or other fluid displacement devices, regardless of the type of cartridge or reservoir employed, piston pumps (e.g., electromagnet pumps), MEMS pumps, peristaltic pumps and any other suitable pumps as well as corresponding drive mechanisms. Exemplary infusion pumps that include a cartridge with a plunger, a fluid displacement device in the form of a plunger pusher, and a drive mechanism are described in U.S. patent application Ser. No. 12/890,207, filed Sep. 24, 2010, and corresponding U.S. patent publication number 2012/0078170, both of which are incorporated by reference in their entireties. The present inventions are also applicable to medicaments such as, for example, drugs to mask pain, chemotherapy and other cancer related drugs, antibiotics, hormones, GLP-1, Glucagon, various other drugs that include large molecules and proteins that may require a high level of delivery accuracy, as well as to relatively high concentration insulin (i.e., U-200 and above) such as U-500 insulin.

As noted above, some ambulatory infusion pumps are intended to be worn on a belt, carried in a pocket, or otherwise supported within a holder of some kind (referred to collectively as "pocket pumps"). Such infusion pumps transfer fluid from a reservoir to an infusion set by way of an elongate tube. Subcutaneous access may be obtained by way of a cannula in the infusion set. Other ambulatory infusion pumps are intended to be adhered to the skin above the delivery site (sometimes referred to as "patch pumps"). Here, the cannula or other subcutaneous access device may extend directly from the infusion device. Given these modes of use, patients typically prefer the device to be as small as possible so it is more comfortable, less obtrusive, and less visible. In addition, patients want a device that is easy and convenient to use.

Figure 1B:
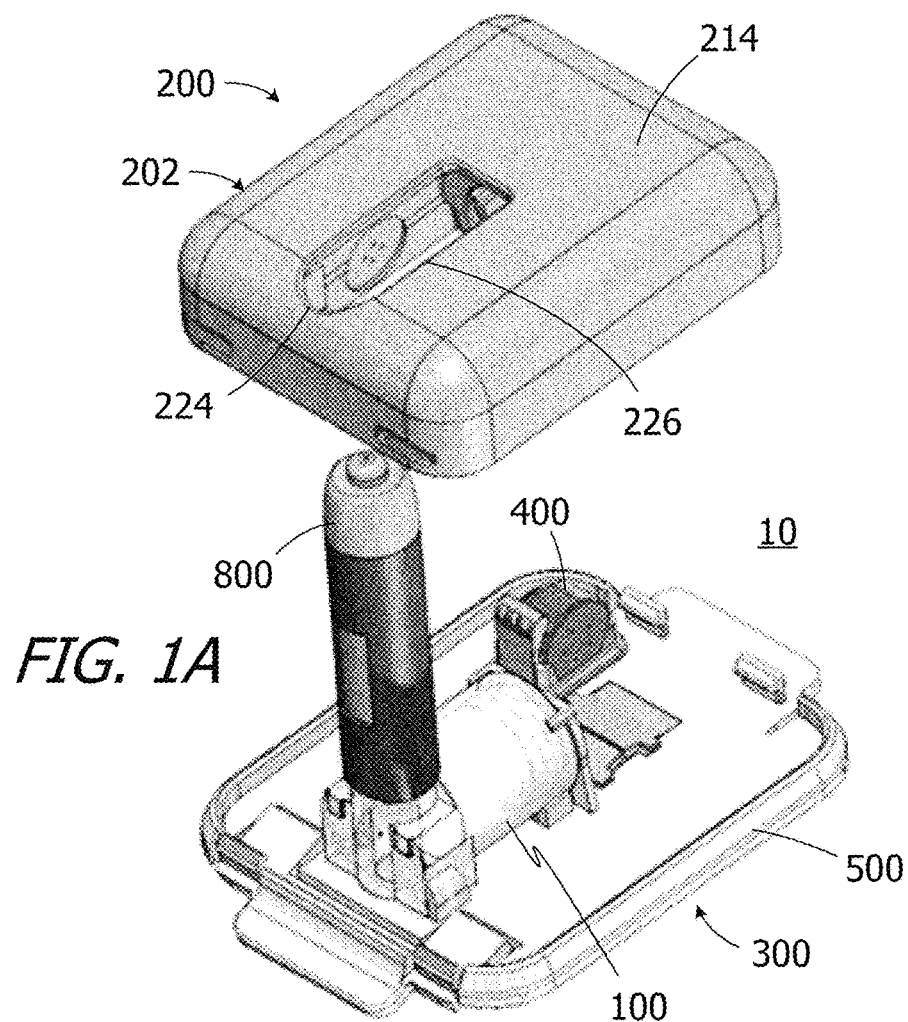
FIG. 1B is a perspective view of a portion of the system illustrated in FIG. 1A in an assembled state with the inserter and associated cannula cap in place.
Figure 1B:
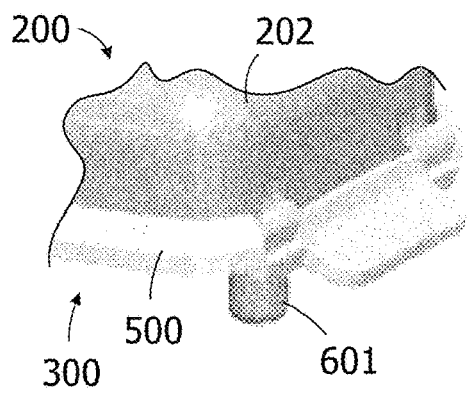
Figure 1C:
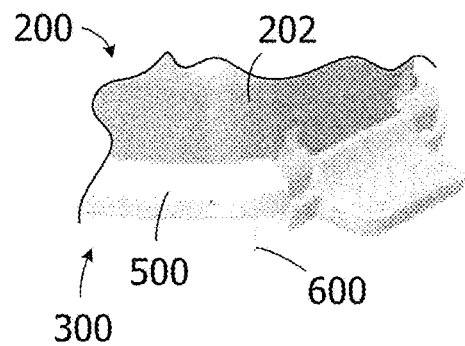
FIG. 1C is a perspective view of a portion of the system illustrated in FIG. 1A with the cannula cap removed and the cannula deployed.

An exemplary ambulatory infusion system, which is generally represented by reference numeral 10 in FIGS. 1A-1C, includes an ambulatory infusion pump assembly (or "pump assembly") 200 and a disposable assembly 300. Exemplary disposable assembly 300 includes a baseplate 500, a medicament cartridge assembly (or "cartridge") 100, a disposable battery or other energy supply 400, a cannula cap 601, and an inserter 800 for inserting a cannula 600. These disposable assembly components may be integrated together into a single package delivered to the user. For instance, the cartridge assembly 100 may be secured to the baseplate 500. Alternatively, some or all of the disposable assembly components may be provided to the user separately, as user-replaceable parts. The disposable assembly 300 may be secured to the pump assembly 200, as shown in FIGS. 1B and 1C. FIG. 1C also shows cannula cap 601 removed, the inserter 800 fired, and the cannula 600 positioned for use. As discussed in greater detail below, the disposable assembly 300 may be configured for different medicaments, such as different medicament concentrations, different medicament amounts, or different modes of system operation.

Referring to FIG. 1A, the exemplary pump assembly housing 202 may be provided with one or more openings. For example, an inserter opening 224 may be provided in the housing top wall 214 to enable access for the inserter 800. Such access may be required for a cannula insertion process, such as that described below with reference to FIGS. 6A, 6B, 10, 10A, 10B, and 11. The top wall 214 of the housing 202 may also be provided with a cartridge opening 226 for the top of cartridge 100. The inserter opening 224 and cartridge opening 226 are merged into a single opening in the embodiment illustrated in FIGS. 1A-1C. Such openings may be separate in other embodiments. Cartridge opening 226 facilitates observation of the medicament and plunger within a cartridge formed from transparent material. Additionally, in the illustrated embodiment, the pump assembly 200 is configured (i.e., sized, shaped, etc.) such that a portion of the associated cartridge (e.g., cartridge 100) may protrude through the cartridge opening 226 when the disposable assembly is attached to pump assembly 200. For example, the relative configurations of the disposable assembly 300, cartridge assembly 100 and pump assembly 200 may be such that the cartridge body protrudes slightly (e.g., about 0.40-1.00 mm, or five percent of the reservoir volume) through the opening 226 in the housing top wall 214. The bulk of the cartridge body will, however, be located below the inner surface of the top wall 214. The length of the cartridge opening 226 is substantially equal to the length of the cartridge reservoir, with appropriate clearance, while the width is somewhat less than the diameter of the cartridge. For example, the width of the opening 226 may be about 60 to 90% of the diameter and is about 83% in the illustrated implementation.

Figure 1D:
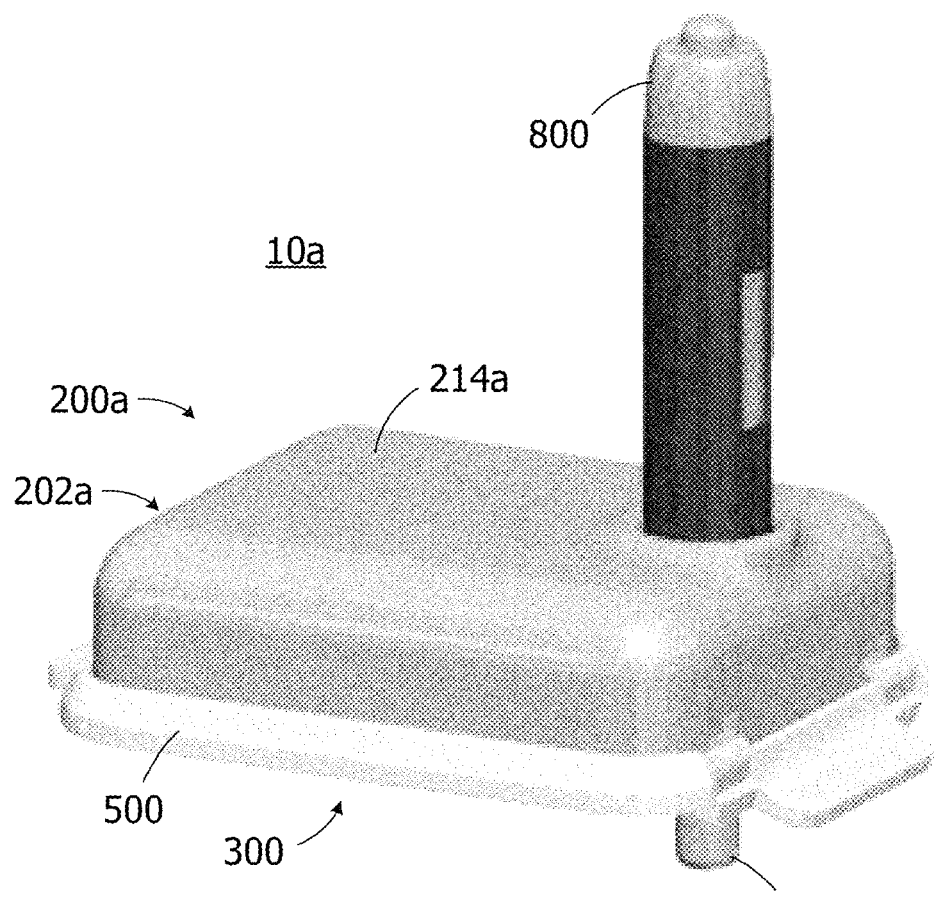
FIG. 1D is a perspective view of another exemplary infusion pump system with the pump assembly attached to the disposable assembly, and with the inserter and cannula cap in place.
Figure 1E:
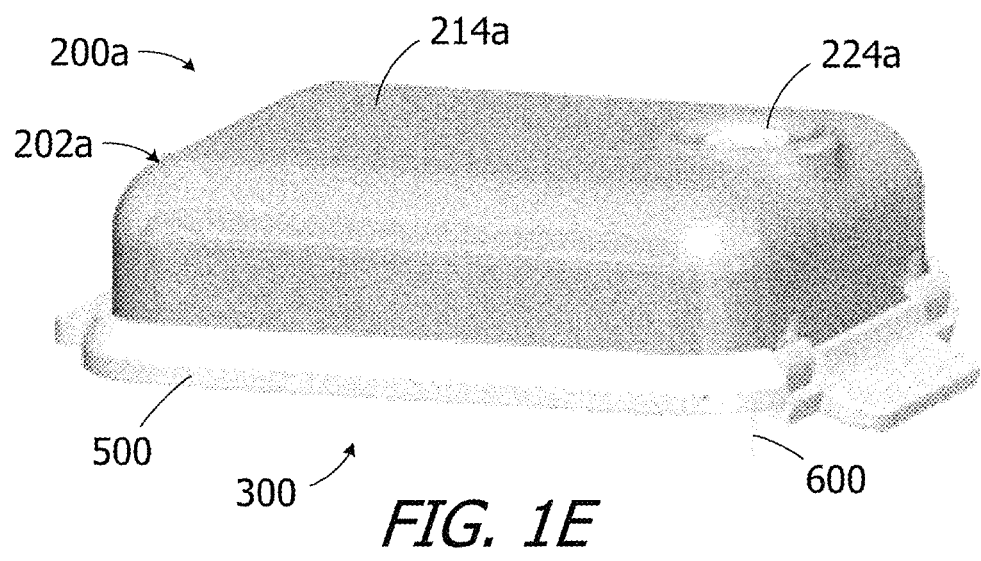
FIG. 1E is a perspective view of the system illustrated in FIG. 1D with the cannula cap removed, the cannula deployed, and the inserter fired and removed.

In other implementations, the cartridge opening 226 may be omitted. To that end, and referring to FIGS. 1D and 1E, the exemplary system 10a is essentially identical to system 10 and similar elements are represented by similar reference numerals. The pump assembly 200a includes a housing 202a with a top wall 214a, and the top wall includes an inserter opening 224a. Here, however, the top wall 214 does not include a cartridge opening and the cartridge 100 is located within the housing 202a.

Figure 2A:
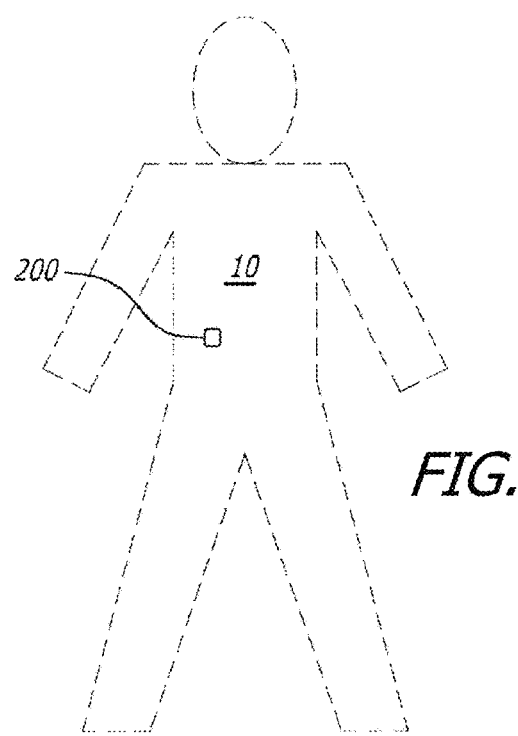
FIG. 2A is a schematic view showing use of an exemplary infusion pump system.
Figure 2B:
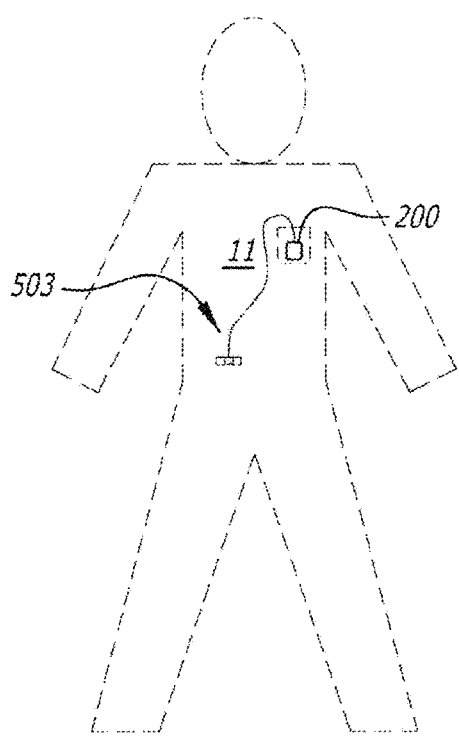
FIG. 2B is a schematic view showing use of an exemplary infusion pump system.
Figure 2C:
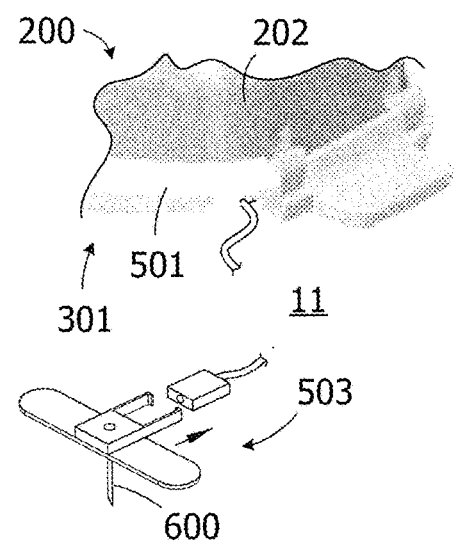
FIG. 2C is a perspective view of a portion of the exemplary infusion pump system illustrated in FIG. 2B.

As discussed in U.S. patent publication number 2012/0078170, ambulatory infusion systems that employ a cartridge, a pump assembly, and a baseplate may be configured for different types of use. For example, the disposable assembly 300 may be adhered to the patient's skin and may be used in conjunction with a cannula 600 that is operatively connected to the cartridge assembly 100 so that the system 10 may be deployed as a "patch-pump," as shown in FIG. 2A. Alternatively, as shown in FIGS. 2B and 2C, the baseplate 501 of disposable assembly 301 may be configured to connect the cartridge assembly 100 to an infusion set 503 (e.g., by way of the illustrated infusion set tube and connector arrangement) so that the system 11 may be deployed as a "pocket pump," a "belt-worn pump" or some other wearable pump. In yet another alternative, the baseplate may be a medicament non-delivery baseplate that may be used to seal the cartridge 100 during periods of non-use, thereby defining a non-use system (not shown). In other words, using the same pump assembly (e.g., pump assembly 200), the user may configure the system for use as "pocket pump" or a "patch pump" by simply selecting the appropriate disposable assembly and attaching the disposable assembly to the pump assembly. The user may also switch from one configuration to another, by simply removing one disposable assembly and replacing it with another disposable assembly.

It should therefore be noted that the present inventions include kits that contain various combinations of baseplates, at least two of the baseplates being different. Additionally or alternatively, kits or other packages may include various disposable assembly components, such as medicament cartridges and/or cannula inserter, as user replacements. Kits may also include a pump assembly. The disposable assemblies in such kits may also include the detection/identification instrumentalities discussed below. The components of the present kits (e.g., combination of various disposable assemblies and/or components) may be stored in a common package, with individual packages for each component if necessary, and provided to the user in the common package. Other components that may be provided in such kits include, but are not limited to, inserters that are preloaded with a cannula, and cleaning swabs. A recharger may also be provided in a kit that includes a pump assembly.

In addition to disposable assembly packaging and labeling, the different disposable assemblies may include visual cues to differentiate the various disposable assemblies. For instance, disposable assemblies with different concentrations of medicament or different medicament fill volumes may use different colors for the cartridge and/or baseplate of the disposable assembly.

It should also be noted here that, but for the issue of priming, the dispensing procedures associated with an infusion system "patch pump" configuration, which may include a pump assembly 200 and a disposable assembly 300, are substantially the same as the dispensing procedures associated with a "pocket pump" configuration, which may include a pump assembly 200 and a disposable assembly 501 (see FIGS. 2B and 2C). With a "patch pump" configuration, priming is not necessary because the volume of the associated cannula will be very small and there is a direct connection between the cannula and the medicament cartridge. Priming is, however, required to fill the infusion set tube (FIG. 2B) in a "pocket pump" configuration prior to the onset of medicament delivery. For instance, 20-30 μl may be required to fill the entire infusion set tube and, accordingly, the priming procedure may involve the rapid delivery of 10-15 IUs of U-500 insulin to the tube. The present inventors have determined that it would be advantageous to prevent users from initiating a priming procedure when the system is in the "patch pump" configuration, with a cannula positioned to deliver medicament essentially directly from the medicament cartridge to the patient, because rapidly delivering 10-15 IUs of insulin to the patient could adversely affect patient health.

To prevent such undesirable outcomes, and for user convenience in other situations involving the choice between a variety of disposable assemblies (such as disposable assemblies with cartridges containing different medicaments, different concentrations of a medicament, and/or varying amounts of medicaments), at least some of the present disposable assemblies may be provided with a baseplate identification device and at least some of the present pump assemblies may be provided with structure that cooperate with a baseplate identification device in such a manner that the pump assembly controller can make a "baseplate type" determination. Exemplary baseplate identification instrumentalities and methodologies may be as described in U.S. patent application Ser. No. 12/890,207, filed Sep. 24, 2010 and corresponding U.S. patent publication number 2012/0078170, as well as in aforementioned U.S. patent application Ser. No. 61/415,830, filed Nov. 20, 2010.

Alternatively, the patient or a clinician may program the system, such as via a remote control, to indicate the type of disposable assembly attached. In a manner such as this, a patient can access a variety of medicaments for use with a single pump assembly.

Once the "baseplate type" determination is made (e.g., "patch pump" disposable assembly 300 versus a "pocket pump" disposable assembly 301), the pump assembly will proceed in a manner, or mode of operation, that is appropriate for the attached disposable assembly. For example, if "patch pump" disposable assembly 300 is detected, the pump assembly controller will not include priming as part of the delivery process and, in some implementations, will prevent the user from manually implementing a priming procedure. If, on the other hand, a "pocket pump" disposable assembly 301 is detected, then the delivery process may include appropriate priming of the infusion set tube.

Whether configured as a "pocket pump" or a "patch pump," the system may be configured to provide basal delivery of medicament in accordance with a delivery profile provided by a physician by way of a clinician's programming unit. For example, the system may include a program that stores a number of delivery profiles (e.g., delivery profiles associated with a 24-hour delivery cycle, delivery profiles for particular situations such as sleep or illness, and the like). Each delivery profile specifies multiple doses (or pump "operations") over time, e.g., a particular number of doses at particular times or a particular number of doses per unit time. In some implementations, a dose may be the volume associated with the minimum controllable displacement of a cartridge plunger. The system may also be configured to provide bolus delivery in response to an instruction from a patient remote control. A bolus instruction may come in response to a high glucose level measurement in the case of a diabetic patient, an increase in pain level in the case of a pain management patient, or some other symptom. The system may also be configured to perform other functions, such as ending medicament delivery in response to instructions from a patient remote control.

The present infusion pumps may be used in conjunction with a wide variety of remote controls. Such remote controls may be used to, for example, allow the user to transmit instructions to the pump assembly or facilitate communication between the pump assembly and the user (e.g., an alarm condition message or other message concerning the conditions of the pump assembly). An exemplary remote control 1000 (FIG. 12) may be configured to facilitate one, some, or all of the following operations: (1) turning the remote control 1000 on or off, (2) associating (or "assigning") the remote control 1000 to the pump assembly 200, (3) obtaining status information such as medicament level, battery charge level, and/or alarm conditions, (4) silencing the pump assembly alarm, (5) selecting options that may be associated with the pump assembly alarm such as type of alarm (audible, palpable, and/or visible) and strength/volume of alarm, (6) connecting the remote control to a computer to, for example, update remote control or pump assembly firmware, load and delete delivery profiles stored in the pump assembly or remote control, and otherwise reprogram the pump assembly or remote control, (7) selecting medicament options such as medicament concentrations, (8) selecting and initiating a stored medicament delivery profile, (9) increasing and decreasing medicament dose rate, (10) retracting the plunger pusher from the cartridge to the home position, and/or (11) pausing a dispensing operation. A user may pause delivery in order to remove or replace a patient applied structure (e.g., a disposable assembly), adjust for a current or anticipated changed body condition (e.g., low glucose, vigorous exercise), follow a physician's suggestion, or disconnect the pump assembly from the body for any other reason.

The exemplary remote control 1000 (FIG. 12) may be configured to generate an indicator, based on information from a controller for pump assembly 200, that is indicative of the amount of time remaining in the current dispensing program and/or the amount of time until the next disposable assembly replacement and/or the amount of time until the pump assembly battery requires recharging. The indicator may be audible, visible, palpable, or combinations thereof. A time remaining indicator may be useful for a variety of reasons. For example, knowledge of the time remaining prior to next disposable assembly replacement allows the patient to determine, based at least in part on the current time of day and upcoming events (e.g., travel or sleep), whether or not it would be more convenient to replace the disposable assembly at a time prior to the end of the dispensing program.

As described above, parts of the present systems may be considered the reusable parts, while other parts may be considered the disposable parts. In the illustrated embodiments, the pump assembly 200, which includes structures such as the motor and various mechanical structures, the pump assembly controller, and a rechargeable battery, is reusable, while exemplary disposable assemblies 300 and 301, which may include the baseplate 500 and 501, the cartridge assembly 100, the disposable battery 400, the cannula 600, and the cannula inserter 800, are disposable.

With respect to dimensions, some embodiments of the exemplary pump assembly 200 may have the following dimensions: length dimensions of 42 mm+/−1.0, 42 mm+/−0.10, 40+/−1.0 mm, 40+/−0.10 mm or 40+/−5.0 mm; width dimensions of 34 mm+/−1.0, 34 mm+/−0.10 mm, 32 mm+/−1.0 mm, 32 mm+/−0.10 mm or 32 mm+/−5 mm; overall thickness or height dimensions of 11 mm+/−1.0 mm or 11 mm+/−0.10 mm; and wall thickness dimensions on the order of 1.0 mm+/−0.10 mm. Suitable pump assembly housing 202 materials include, but are not limited to, plastic or other materials having a modulus of elasticity of 0.2-1.0 million psi.

The dimensions of the disposable assembly 300 may correspond to those of the associated pump assembly 200. In the context of the exemplary pump assembly 200 described above, the baseplate 500 may be 1 mm thick, with length/width relationships such as 42 mm×34 mm, 40 mm×32 mm, and/or 39.0-43.0 mm×31.0-35.0 mm.

Exemplary pump assemblies; pump modules; pump assembly controllers and associated circuitry; rechargeable batteries and associated battery rechargers and recharging methods; battery and recharging management; temperature sensors; operation of the pump module's drive mechanism and plunger pusher for engaging the cartridge plunger; and exemplary alarms and alarm conditions are described in more detail in aforementioned U.S. patent application Ser. No. 61/415,830, U.S. application Ser. No. 13/300,574 and U.S. patent publication number 2012/0078170.

The exemplary system is, as noted above, a cartridge-based system in that medicament cartridge assemblies 100 (which may be included as part of disposable assembly 300) are inserted into the pump assembly 200 and later removed from the pump assembly. The cartridges may also be, but are not required to be, prefilled and disposable. Prefilled cartridges are advantageous for a variety of reasons. By way of example, but not limitation, some users prefer to avoid cartridge filling procedures because they are inconvenient and tend to involve needles. User-based refilling also increases the likelihood that air bubbles will be introduced into the cartridge, while prefilling by the manufacturer of the cartridge and/or the medicament can be accomplished without any substantial introduction of air bubbles using, for example, a vacuum filling procedure. A variety of exemplary medicament cartridges and cartridge assemblies 100, including pressure sensors (such as for sensing occlusion) and other sensors, are described in more detail in U.S. patent publication number 2012/0078170 and aforementioned U.S. patent application Ser. No. 61/415,830 and U.S. application Ser. No. 13/300,574.

Figure 3:
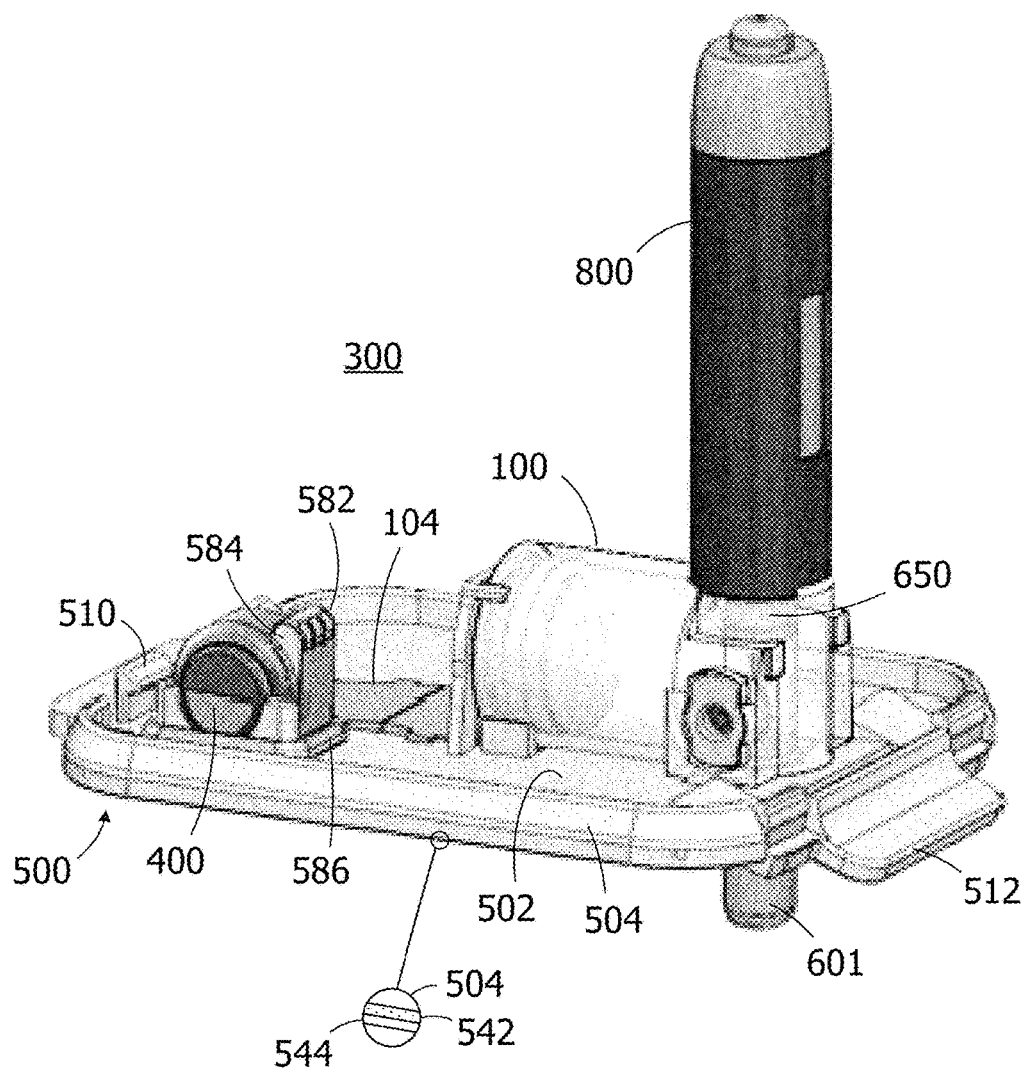
FIG. 3 is a perspective view of an exemplary disposable assembly.

Turning now to FIG. 3, the exemplary disposable assembly 300 includes the baseplate 500, the removable automatic cannula inserter 800, the removable cannula cap 601, the cartridge assembly 100, a cartridge assembly locking mechanism 104, the disposable battery 400, and a flex circuit 582 used to connect the disposable battery to contacts within the pump assembly 200. The exemplary baseplate 500 includes a plate member 502, a wall member 504, an adhesive backing 542 for attachment to the patient, and a removable adhesive cover 544. The baseplate 500 may also be molded with baseplate locking features 510 that snap onto the pump assembly 200, and may also include baseplate removal features 512 to facilitate removal of the pump assembly 200 from the baseplate after the two have been removed from the patient.

Figure 6A:
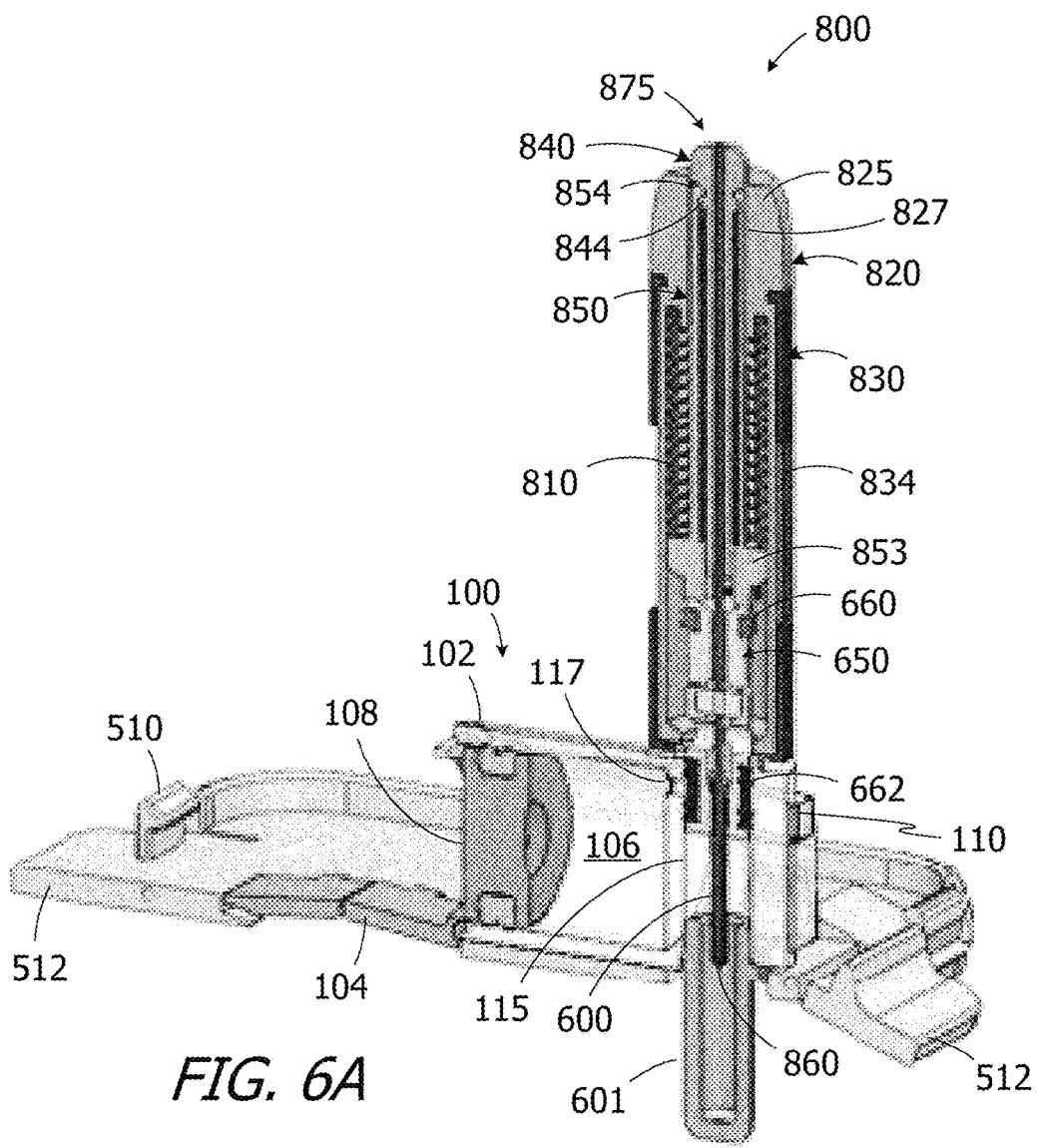
FIG. 6A is a section view of the disposable assembly illustrated in FIG. 3, before inserter firing.

Referring to FIG. 6A, the exemplary cartridge assembly 100 includes a barrel 102 that defines a reservoir 106, a plunger 108 within the barrel, and a manifold 110. The manifold 110, which includes a through-bore 115 and a medicament outlet 117, may be used to connect the reservoir to a cannula in the manner described below. The plunger 108 moves within the cartridge assembly 100 to vary the volume of medicament within the reservoir 106. Cartridge assembly 100 may be, for instance, prefilled with U-500 insulin in various volumes to suit the patient use profile. It may be a syringe design with an on-board occlusion sensor for use with a cannula assembly 650, such as described further below. Cannula cap 601 is attached to the cartridge assembly 100 to maintain a sterile cannula 600 until use. The patient removes cannula cap 601 prior to use.

Figure 4:
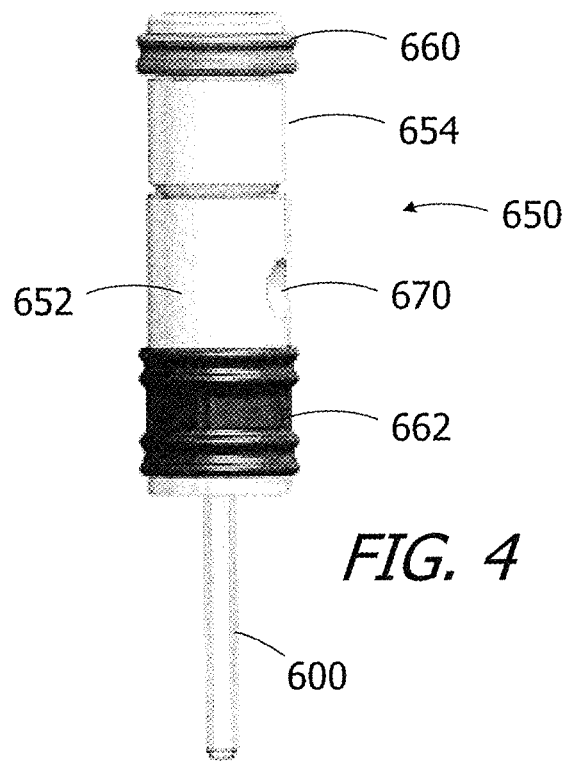
FIG. 4 is a front view of an exemplary cannula assembly.

The cartridge assembly locking mechanism, such as the exemplary cartridge locking mechanism 104 illustrated in FIG. 4, may be a simple toggle (knee joint) mechanism or other mechanism, such as one or more leaf springs, that biases and locks the cartridge assembly 100 into the pump assembly 200 during operation. During attachment of the disposable assembly 300 to the pump assembly 200, the cartridge assembly locking mechanism 104 positions the cartridge assembly 100 tightly into operating position. Other examples of cartridge assembly locking mechanisms are disclosed in U.S. patent publication number 2012/0078170.

The disposable battery 400 may be a commercially available battery, such as a commercially available zinc-air battery, used to charge a battery in the pump assembly, such as an on-board Lithium Polymer battery. The disposable battery 400 may also be selected to have sufficient capacity to operate the system for certain delivery amounts or delivery times, such as for over 400 units of delivered insulin.

As mentioned above, the flex circuit 582 makes electrical contact with the pump assembly 200. In some alternatives, the flex circuit 582 also provides electrical means for identifying the specific type of disposable assembly (e.g., disposable assembly 300 or 301), as is discussed above, including aspects of the disposable assembly such as different medicament fill volumes within cartridge assembly 100, which corresponds to the amount of medicament used in the disposable assembly lifetime. The baseplate 500 may also contain a bias feature 584 to cause forced contact between the electrical contacts on the flex circuit and the pump assembly electrical contacts. Additionally, a gasket 586 may be used to waterproof the contacts.

Additional exemplary baseplates for use with the disposable assemblies of the present inventions, as well as additional exemplary cannula designs, fluidic connection between a medicament cartridge and the cannula, cooperation between the cannula and disposable assemblies (for instance, to prevent axial movement of the cannula relative to the baseplate and patient), attachment of an infusion set to the cartridge of the disposable assembly, configurations and uses of a non-delivery baseplate, arrangements and structures for attaching baseplate and pump assemblies, skin adhesive designs, occlusion sensors, and various inserters may be as described in U.S. patent application Ser. No. 12/890,207, filed Sep. 24, 2010 and corresponding U.S. patent publication number 2012/0078170.

Figure 4A:
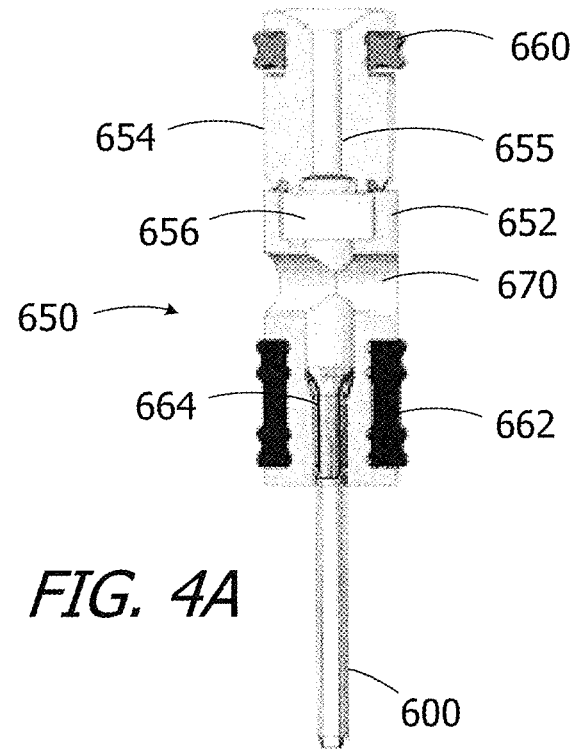
FIG. 4A is a section view of the exemplary cannula assembly illustrated in FIG. 4.

Turning to FIGS. 4 and 4A, the exemplary cannula assembly 650 includes a cannula body 652, a cannula top 654, a trocar septum 656, a top seal 660, a primary seal 662, a funnel 664, and the cannula 600. The cannula body 652 and cannula top 654, which include respective portions of a trocar lumen 655, may be attached via ultra-sonic welding to be concentric and provide operating compression to the trocar septum 656. The funnel 664 attaches the cannula 600 to cannula body 652, and also acts as a guard to guide the trocar into cannula 600, thereby minimizing the chance of wall puncture during manufacturing. A through-hole 670 allows medicament to pass from cartridge assembly 100 into cannula 600 (see FIGS. 10A and 10B).

FIG. 5 shows the exemplary automatic cannula inserter 800 prior to firing, and the following inserter components are shown individually and respectively in FIG. 5A-5D: inserter main body 820, inserter rotation collar 830, inserter trocar hub 840, and spring retainer 850. The exemplary main body 820 (FIG. 5A) includes a tubular portion 821, a pair of pivotable locking features 822 that are respectively located in apertures 823 (only one of each visible in FIG. 5A), an annular groove 824, an enlarged top portion 825, and a central lumen 826. The main body 820 also has a locking surface 827 (FIG. 6A). The exemplary rotation collar 830 (FIG. 5B), which functions as an actuator in the manner described below, includes a tubular portion 831, a pair of lugs 832 at one end separated by gaps 833, and a pair of apertures 834 that extend through the tubular portion. The rotation collar 830 has an annular protrusion 835 (FIG. 6B) at the other end that fits into the annular groove 824 to rotatably secure the rotation collar 830 to the main body 820. The exemplary trocar hub 840 (FIG. 5C) includes a pair of longitudinally extending arms 841 with a pair of stopping features 842 at one end and a top portion 843 at the other, a pair of locking features 844 (only one visible in FIG. 5C), and a center trocar tube 845. The stopping features 842 are separated by gaps 846, and there is an annularly-shaped spring storage region 847 between the arms 841 and the center trocar tube 845. The exemplary spring retainer 850 (FIG. 5D) includes a pair of longitudinally extending arms 851. An abutment 853 is located near one end of the arm 851 and locking features 854 are located at the other end. A lower gap 855 is located between the portions of the arms 851 below the abutment 853 and an upper gap 856 is located between the portions of the arms 851 above the abutment. It should also be noted that the arms 841 and 851 abut one another and together form a cylindrical structure (FIG. 7). The inserter components, as well as the interaction therebetween, are discussed in greater detail below.

Figure 6B:
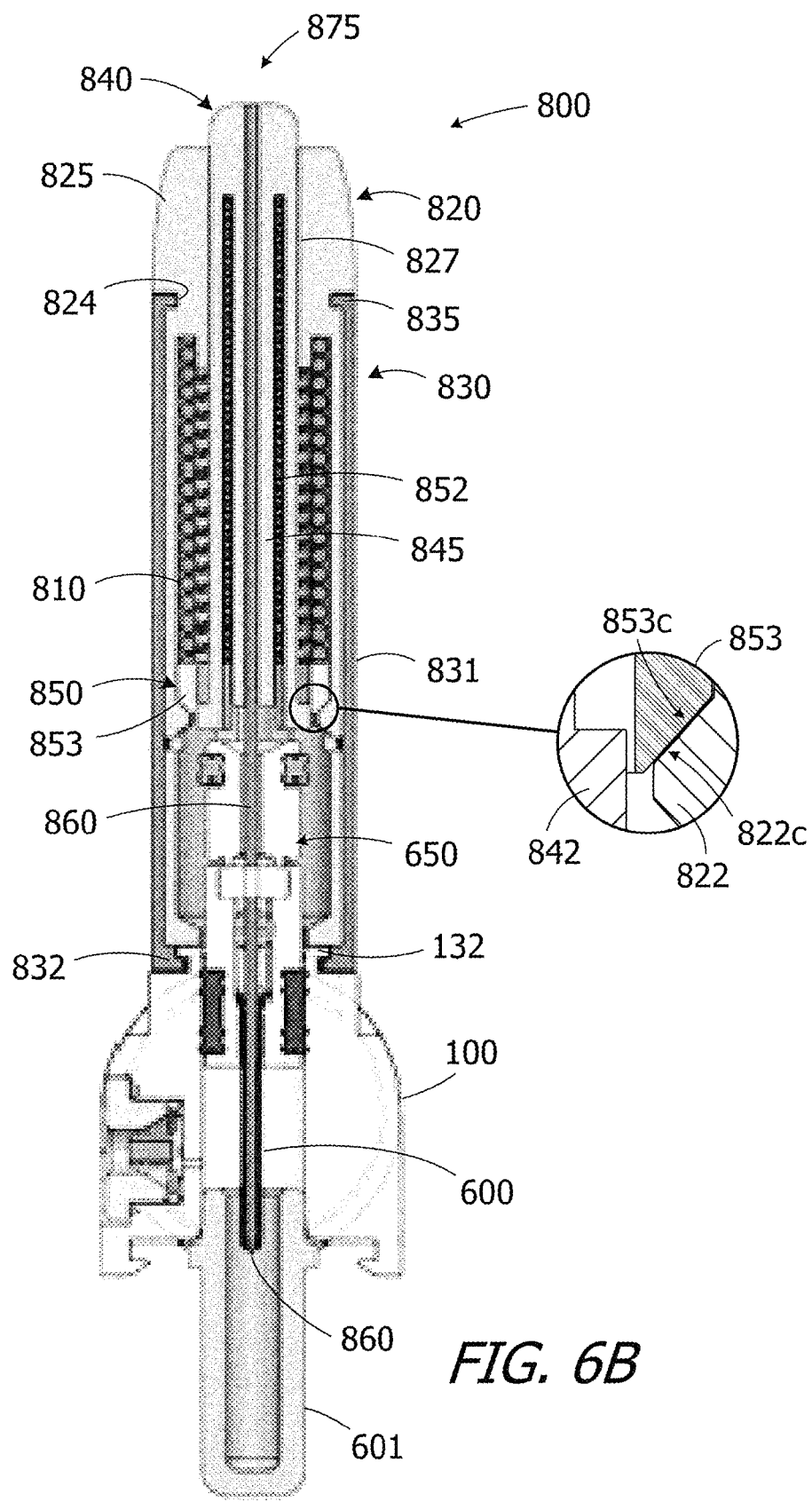
FIG. 6B is a section view, offset 90 degrees from the orientation illustrated in FIG. 6A, of some of the components illustrated in FIG. 6A.
Figure 7:
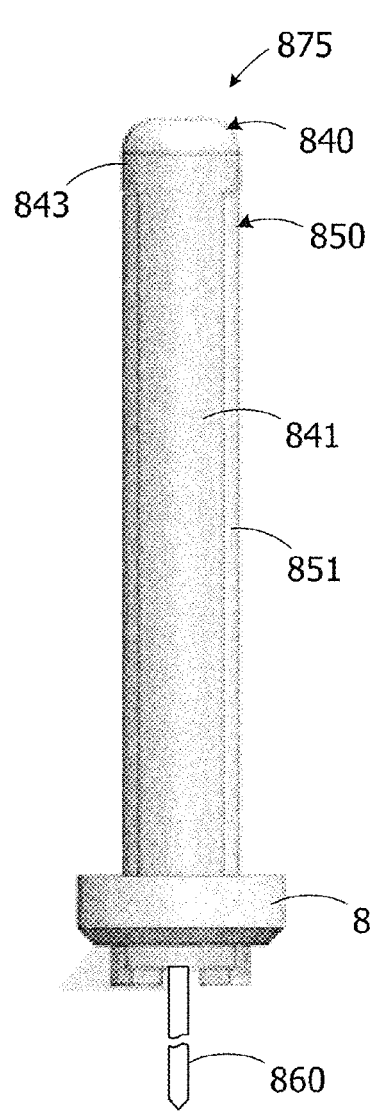
FIG. 7 is a front view of an exemplary slide assembly of an exemplary automatic cannula inserter.

FIG. 6A shows a cross section of an exemplary disposable assembly 300 before the firing of the inserter 800, while FIG. 6B shows a cross section view of the inserter 800 that is offset 90 degrees from the view in FIG. 6A. FIGS. 6A and 6B show the components of the inserter 800 in their pre-fired (or "storage") conditions, as well as the cannula cap 601 and the cannula assembly 650 in its pre-fired position. The apertures 834 on the rotation collar 830 are rotationally offset from (i.e., are not rotationally aligned with) the locking features 822 on the main body 820 (FIG. 6A), and the angled surfaces 822c (i.e., surfaces that are not perpendicular to the longitudinal axis of the inserter) on the locking features 822 are engaging the angled surfaces 853c on the underside (or "locking feature") of the abutment 853 of the spring retainer 850 (FIG. 6B). The tubular wall 831 of the rotation collar 830 prevents the locking features 822 from pivoting out of engagement with the abutment 853. As such, and despite the force being applied to the abutment 853 by a compressed resilient member such as exemplary spring 810 (or other compressed or stretched member that stores potential energy until it is released), the angled surfaces 822c on the locking features 822 will not slide out of contact with the angled surfaces 853c on the abutment. In addition, the locking features 854 on the spring retainer 850 are engaging the locking features 844 on the trocar hub 840 (FIG. 6A) because the main portion locking surface 827 prevents the locking features 844 and 854 from separating, thereby preventing movement of the trocar hub 840 relative to the spring retainer 850, as is discussed below with reference to FIGS. 7 and 7A. The rotation collar lugs 832 are engaging the cartridge lugs 132 (FIG. 6B), thereby preventing separation of the inserter 800 from the cartridge 100.

Figure 7A:
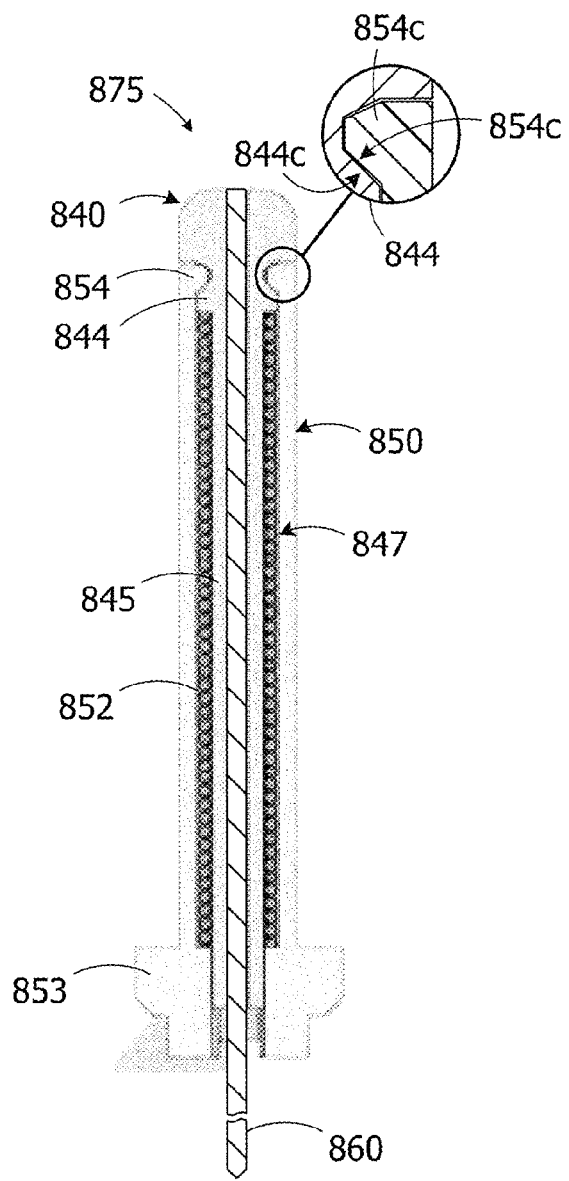
FIG. 7A is a section view of the slide assembly illustrated in FIG. 7.

FIGS. 7 and 7A show an exemplary slide assembly (or "trocar assembly") 875 of exemplary inserter 800 in greater detail. Exemplary slide assembly 875 consists of four parts: the trocar hub 840, the spring retainer 850, a compresses resilient member such as exemplary trocar spring 852 (or other compressed or stretched member that stores potential energy until it is released), and the trocar 860. The trocar spring 852 is compressed between the spring retainer abutment 853 and the trocar hub locking features 844. Referring more specifically to FIG. 7A, the locking features 844 and 854 on the trocar hub 840 and the spring retainer 850 include angled surfaces 844c and 854c that allow the trocar hub and spring retainer to separate from one another in the manner described below. Before firing of the inserter 800, the spring retainer locking features 854 engage trocar hub locking features 844, thereby locking the trocar hub 840 and spring retainer 850 to one another, which in turn resists the extension force of the compressed trocar spring 852. The locking features 844 and 854 are held together when slide assembly 875 is located within inserter main body locking surface 827 (FIGS. 6A and 6B), as described further below in conjunction with the action of inserter 800 that occurs when a user activates the firing of cannula 600.

At the most basic level, use of the exemplary infusion pump systems (e.g., systems 10, 10a or 11 in FIGS. 1A-2C) involves obtaining a new disposable assembly 300 (or 301, etc.), connecting the disposable assembly to the pump assembly 200, peeling the liner from the baseplate adhesive layer, gaining subcutaneous access, and initiating a medicament delivery operation. In some instances, use may involve additional steps such as removing the cover from disposable battery 400 or removing a cannula cap 601 from the disposable assembly, if necessary. Various aspects of the basic operation of the present systems are described below. Operation of a system does not necessarily require all of the steps each time the system is deployed, and the order of some of the steps may be changed. Operation is also discussed below, in the exemplary context of the above-described pump assembly 200 and patch pump disposable assembly 300, through the use of a flow chart (FIG. 8) as well as through illustrations of exemplary systems and methods of use in various states (FIGS. 6A, 6B, 9, 10, 10A, 10B, 11, and 12). The discussion is, however, equally applicable to other patch pump implementations, as well as to pocket pump implementations with minor variations. Also, unless otherwise indicated, the actions and determinations performed by the pump assembly 200 are controlled by the pump assembly controller and further references to the controller are omitted in the interest of brevity.

Referring first to FIG. 8, use of the present systems may involve removal of a disposable assembly from a pump assembly and the replacement of some or all of the disposable assembly. This may occur (in some instances automatically) when the medicament cartridge is empty (as described in more detail in U.S. patent application Ser. No. 12/890,207 and corresponding U.S. patent publication number 2012/0078170) (Step S101) and a "replace disposable assembly" message or alert is presented (Step S102), or when the pump assembly controller receives a user-initiated "replace disposable assembly" signal from the remote control 1000 (Step S103). The user may desire to replace a disposable assembly before the medicament cartridge is empty for a variety of reasons such as, for example, to accommodate the user's sleep or travel schedule, when the medicament appears cloudy or otherwise exhibits a loss of effectiveness, when a dispensing problem arises, or due to a prescribed change in medicament. As described in U.S. patent application Ser. No. 12/890,207 and corresponding U.S. patent publication number 2012/0078170, the system will automatically or via user-initiation prepare for separation of the disposable assembly from the pump assembly (e.g., a pusher that pushes a plunger in cartridge 100 will retract to home position, Step S104). The user may then obtain, possibly from storage in a refrigerator depending on medicament requirements, a new disposable assembly 300 (containing cartridge 100, disposable battery 400, baseplate 500, cannula 600, and inserter 800) and the remote control 1000 (if not already at hand) (Step S105). The pump assembly 200 and disposable assembly 300 may then be removed from the skin, separated, and the disposable assembly 300 discarded (Steps S106 and S107).

Next, if necessary, the cover may be removed from disposable battery 400 (Step S108) and the new disposable assembly 300 may then be attached to the pump assembly 200 (Step S109). Next, a pusher zeroing procedure (Step S110), described in detail in U.S. patent application Ser. No. 12/890,207 and corresponding U.S. patent publication number 2012/0078170, may be user-initiated or may be an automatic aspect of pump operation. If the results of the zeroing procedure are negative, the pusher is withdrawn from the cartridge, the disposable assembly 300 or at least medicament cartridge 100 is removed and discarded, a new disposable assembly or cartridge is inserted, and the zeroing procedure is repeated (Steps S111, S112, S113 and S114). Alternatively, if the results of the zeroing procedure are positive, the pusher may withdraw from cartridge 100 (Step S115), as described in U.S. patent application Ser. No. 12/890,207 and corresponding U.S. patent publication number 2012/0078170.

The user should clean the skin surface S onto which the baseplate 500 of disposable assembly 300 will be adhered (FIG. 9, and Step S116 of FIG. 8). Then the user removes cannula cap 601 (if present) and peels off baseplate adhesive liner 544 to expose a baseplate adhesive layer 542 (Step S117).

At this point, and as shown in FIGS. 6A and 6B, cannula assembly 650 is in its initial position prior to insertion of the cannula 600 via firing of exemplary cannula inserter 800. Here, the trocar hub 840 is secured to the spring retainer 850, and the main body 820 is secured to the spring retainer 850. The rotation collar 830 is preventing the main body 820 and the spring retainer 850 from moving relative to one another, and is also preventing the trocar hub 840 and the spring retainer 850 from moving relative to one another in that the locking features of the trocar hub 840 and spring retainer 850 will remain engaged until the locking features move past the locking surface 827.

Figures 10, 10A:
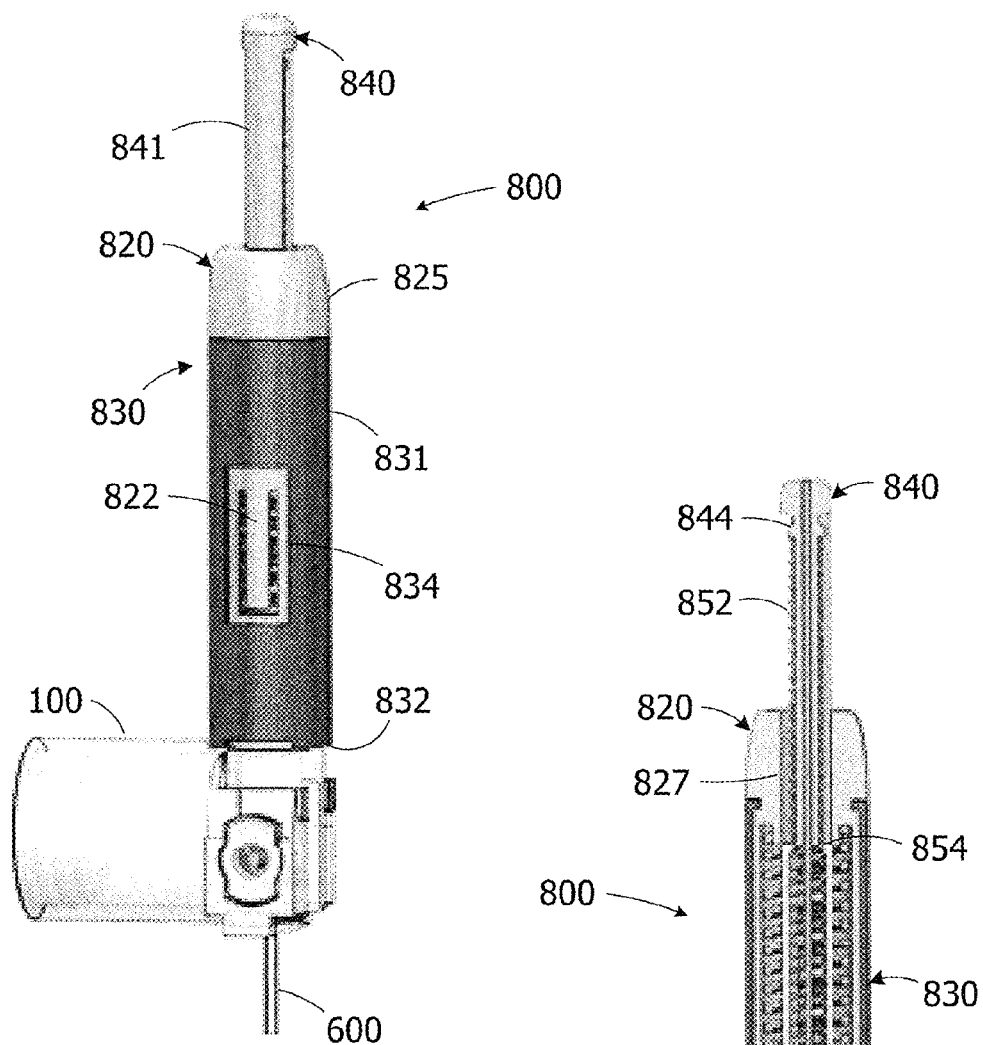
FIG. 10 is a perspective view of some of the components illustrated in FIG. 6A, after inserter firing.
FIG. 10A is a section view of the components illustrated in FIG. 10.

As noted above, the exemplary inserter 800 includes a slide assembly 875 within the main body 820, and an actuator, such as the rotation collar 830. The rotation collar 830 releases the compressed spring 810 or other biasing device to insert cannula 600. For instance, as shown in FIG. 10, the locking features 822 on the inserter body 820 may be released from the spring retainer 850 by rotation of the rotation collar 830 that aligns the apertures 834 with the locking features 822. In particular, such alignment allows the locking features 822 to pivot away from the spring retainer abutment 853. The release of the inserter body locking features 822 allows the angled surface 853c on the spring retainer 850 to slide past the angled surfaces 822c, thereby allowing main spring 810 (FIGS. 6B and 10B) to extend and drive the trocar hub 840, spring retainer 850 and other elements of the slide assembly 875 downwardly (in the illustrated orientation) to insert the cannula 600, as described further below.

As noted above, the trocar 860 is carried on the slide assembly 875. The exemplary cannula assembly 650 is pre-mounted on the trocar 860 such that the sharp distal end of the trocar extends beyond the distal end of cannula 600 (FIG. 6B). In addition, cannula 600 may be initially positioned to provide a seal, such as seal 662, against the medicament outlet 117 of cartridge 100 (FIG. 6A). In these embodiments, the sharp distal end of trocar 860 is entirely within cartridge assembly 100 while in the initial position, prior to cannula deployment, to prevent accidental contact by the user (FIGS. 6A and 6B). Inserter 800 may also be configured to automatically withdraw trocar 860 back into the inserter main body 820 after the cannula is deployed, as described below.

Returning to the steps in FIG. 8, the system including pump assembly 200 and disposable assembly 300 (including cartridge assembly 100, baseplate 500, disposable battery 400, cannula 600, and inserter 800) may be positioned over a suitable body location and pressed gently to adhere the system via adhesive layer 542 to the skin surface S (Step S118).

As shown in conjunction with FIGS. 6A, 6B, 10, 10A, and 10B, exemplary inserter 800 automatically inserts cannula 600 and removes trocar 860. Exemplary inserter 800 may be actuated by rotating inserter collar 830 approximately 60 degrees in either direction to fire the cannula (Step S119). This releases main spring 810 as described above, which extends and drives slide assembly 875 and cannula assembly 650 toward the patient. As slide assembly 875 moves, the locking surface 827 keep the trocar hub locking features 844 and the spring carrier locking features 854 engaged (as shown in FIG. 7A) until cannula 600 is fully inserted and the inserter components are in their "fired" positions. Once slide assembly 875 travels past the end of the locking surface 827 (see FIG. 10A), locking features 844 and 854 disengage, allowing the compressed trocar spring 852 to extend upwards, which removes trocar 860 (which is attached to trocar hub 840) from cannula 600 and withdraws trocar 860 completely into inserter 800. The trocar hub stopping features 842 engage the end of the locking surface 827 to stop trocar hub 840 when it is fully extended (see FIGS. 10, 10A, and 10B).

Returning again to FIG. 8, the inserter is then disengaged (Step S120). In some examples, the patient may disengage the inserter. In the exemplary design illustrated in FIGS. 6A, 6B, 10, 10A, and 10B, the user may continue to rotate inserter collar 830, for instance, a total of 90 degrees. Once rotation collar 830 has been rotated 90 degrees from the pre-fired position, inserter lugs 832 on the rotation collar 830 may disengage from cartridge lugs 132 at the top of cartridge assembly 100 (FIG. 6B). The inserter 800 may then be disposed of.

In some embodiments, the inserter 800 may be about 8 mm diameter, with the main spring 810 providing cannula assembly 650 about 8 mm of travel with a starting force of about 5 lbs. and an ending force of about 4 lbs. The main spring 810 may be made of 0.025 inch diameter music wire, with 17 turns and an outside dimension of 0.226 inch. The trocar spring 852 may provide travel of about 21 mm with a starting force of about 2.5 lbs. and an ending force of 0.88 lbs., and may be made of 0.013 inch diameter music wire, with 48 turns and an outside dimension of 0.0886 inch.

In other examples, the inserter disengages automatically, with no post-insertion user manipulation required. It may be advantageous to reduce or eliminate inserter removal forces because such forces may disturb the adhesive used to attach the system to the user's body or kink the cannula where it enters the body. The exemplary inserter 800' illustrated in FIG. 11 is similar to inserter 800 and similar elements are represented by similar reference numerals. Here, however, the inserter main body 820' flexes outwardly when the inserter 800' is fired, thereby automatically releasing cartridge lugs 132 from inserter lugs 832'. The rotation collar of inserter 800' (not shown) does not extend down to the inserter lugs 832' so as to not interfere with the flexing. With this design, as main spring 810 pushes spring retainer 850' toward cartridge assembly 100, leading edges 851' of spring retainer 850' engage and run along ramps 834', causing the inserter main body 820' to flex and draw the inserter lugs 832' away from cartridge lugs 132. Tests indicate that 0.25 lb. of force causes enough deflection to allow the inserter lugs 832' to disengage, with an acceptable stress level. Thus, once this inserter 800' has finished firing, the cannula 600 is in place, the trocar 860 is retracted, and the inserter 800' is automatically disengaged from cartridge assembly 100. Inserter 800' may then be removed without any manipulation that could disrupt adhesive attachment or cannula positioning.

As best seen in FIGS. 10A and 11, after the cannula is inserted, primary seal 662 is displaced (along with most of the cannula assembly 650) to a position below medicament outlet 117, thereby effectively preventing cannula 600 from withdrawing from the patient. Alternatively, a living hinge or other latch may be employed to prevent cannula 600 from withdrawing from the patient. Additionally, as noted above, in the pre-fired condition, primary seal 662 seals against medicament outlet 117. Once fired, top seal 660 prevents medicament from leaking out the top of the cartridge through-bore 115, while primary seal 662 maintains a leak-free path at the bottom. Medicament flows from the cartridge outlet 117, into the space between the through-bore 115 and the outer surface of the cannula body 652 and cannula top 654, into the through-hole 670, and into the cannula 600.

Returning again to FIG. 8, in some implementations, the pump assembly may be provided with structure (not shown) that determines whether or not the cannula is properly inserted (Step S121). If the cannula is not properly inserted, an error message will be provided to the user (Step S122).

Figure 12:
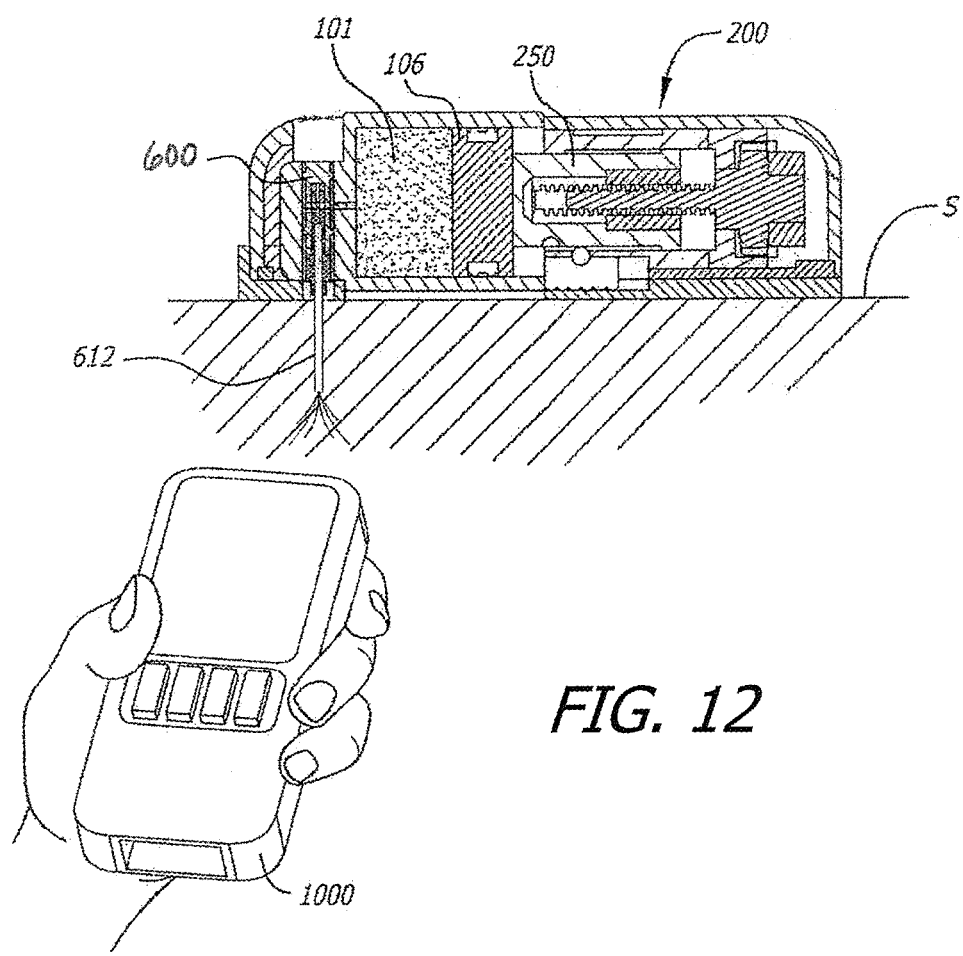
FIG. 12 is a section view showing an exemplary infusion pump system dispensing medicament by way of the cannula in response to commands from a remote control.

Finally, as shown in FIG. 12, if necessary, the remote control 1000 may be used to initiate a particular medicament delivery operation (Step S123). The delivery operation may follow a predetermined delivery profile (e.g. a particular basal rate, a series of time-spaced bolus deliveries, or some combination thereof) that is equated to motor rotations, at particular rates and times, required to deliver medicament in accordance with the profile. The profile may be input by the user with the remote control 1000 and stored by the pump assembly controller. For example, the remote control may store a number of different delivery profiles and bolus deliveries from which the patient can choose. Such profiles may correspond to, for example and depending on the medicament, days where vigorous exercise is expected, days where it is not, incidences of increased pain, etc. Alternatively, or in addition, the profile stored in the pump assembly controller may be set by a clinician's programming unit. In such a case, a remote control may not be needed to initiate, e.g., basal delivery.

The discussion above is also applicable to use of the "pocket pump" system 11. Minor variations in the above-described procedure include, for example, use of disposable assembly 301 with baseplate 501, deploying the infusion set 503 instead of a cannula, and priming of the infusion set tube.

Various methodologies are presented here in the context of the exemplary structures described in the preceding sections, and illustrated in the various figures, for the purpose of explanation only. Although the present methodologies may employ the structures described above, they are not limited thereto. Additionally, the pump assembly may provide audible, visible and/or tactile notifications. A remote control may also provide audible, visible and/or tactile notifications as an alternative to, or in addition to, any notifications provided by a pump assembly. Additionally, embodiments of the present inventions may incorporate any one, combinations of less than all, or all of the methodologies or devices referenced above.

Although the inventions disclosed herein have been described in terms of the preferred embodiments above, numerous modifications and/or additions to the above-described preferred embodiments would be readily apparent to one skilled in the art. It is intended that the scope of the present inventions extends to all such modifications and/or additions and that the scope of the present inventions is limited solely by the claims set forth below or later added.

Finally, with respect to terminology that may be used herein, whether in the description or the claims, the following should be noted. The terms "comprising," "including," "carrying," "having," "containing," "involving," and the like are open-ended and mean "including but not limited to." Ordinal terms such as "first", "second", "third," do not, in and of themselves, connote any priority, precedence, or order of one element over another or temporal order in which steps of a method are performed. Instead, such terms are merely labels to distinguish one element having a certain name from another element having a same name (but for the ordinal term) to distinguish the elements. "And/or" means that the listed items are alternatives, but the alternatives also include any combination of the listed items. The terms "approximately," "about," "substantially" and "generally" allow for a certain amount of variation from any exact dimensions, measurements, and arrangements, and should be understood within the context of the description and operation of the invention as disclosed herein. Terms such as "top," "bottom," "above," and "below" are terms of convenience that denote the spatial relationships of parts relative to each other rather than to any specific spatial or gravitational orientation. Thus, the terms are intended to encompass an assembly of component parts regardless of whether the assembly is oriented in the particular orientation shown in the drawings and described in the specification, upside down from that orientation, or any other rotational variation therefrom.

We claim:

1. An inserter apparatus, comprising:
  a main body defining a proximal end, a distal end and a longitudinal axis;
  a trocar assembly, located at least partially within the main body and movable relative to the main body, including
    a first trocar assembly member movable relative to the main body in a first direction from a storage position to a fired position,
    a second trocar assembly member operably connected to the first trocar assembly member such that the second trocar assembly member is movable with the first trocar assembly member in the first direction from the storage position to the fired position and the second trocar assembly member is also movable relative to the first trocar assembly member in a second direction, opposite the first direction, from the fired position to a withdrawn position,
    a first lock apparatus having a locked state that prevents movement of the first and second trocar assembly members relative to one another and an unlocked state that permits movement of the first and second trocar assembly members relative to one another,
    a first force member, that has a first end that applies force to the first trocar assembly member and a second end that applies force to the second trocar assembly member, that stores potential energy when the first and second trocar assembly members are in the storage position and that drives the second trocar assembly member in the second direction with the stored potential energy when the first lock apparatus is in the unlocked state, and
    a trocar carried by the second trocar assembly member;
  a second force member, operably connected to the main body and to the trocar assembly, that applies a force in the first direction to the first trocar assembly member;
  a second lock apparatus having a locked state that prevents movement of the trocar assembly relative to the main body and an unlocked state that permits movement of the trocar assembly relative to the main body; and
  an actuator carried by the main body and rotatable about the longitudinal axis relative to the main body from a first position, that prevents the second lock apparatus from being in the unlocked state, to a second position that allows the second lock apparatus to be in the unlocked state.

2. An inserter apparatus as claimed in claim 1, wherein the second force member drives the second lock apparatus from the locked state to the unlocked state, and drives the trocar assembly from the storage position to the fired position, when the actuator is in the second position.

3. An inserter apparatus as claimed in claim 2, wherein the first lock apparatus is in the locked state when the trocar assembly is in the storage position;
  the first lock apparatus transitions from the locked state to the unlocked state in response to the trocar assembly reaching the fired position; and
  the first force member drives the second trocar assembly member to the withdrawn position when the first lock apparatus transitions from the locked state to the unlocked state.

4. An inserter apparatus as claimed in claim 3, wherein
the main body includes a locking surface that prevents the first lock apparatus from being in the unlocked state when the first lock apparatus is longitudinally aligned with the locking surface;
the first lock apparatus is longitudinally aligned with the locking surface when the trocar assembly is in the storage position; and
the first lock apparatus is not longitudinally aligned with the locking surface when the trocar assembly is in the fired position.

5. An inserter apparatus as claimed in claim 2, wherein
the second force member defines first and second longitudinal ends;
the first longitudinal end of the second force member engages the main body;
the second longitudinal end of the second force member engages the first trocar assembly member; and
the second longitudinal end of the second force member does not engage the second trocar assembly member.

6. An inserter apparatus as claimed in claim 1, wherein
the main body includes a tubular portion; and
the second lock apparatus is carried by, and is pivotable relative to, the main body tubular portion.

7. An inserter apparatus as claimed in claim 6, wherein
the actuator comprises a tubular portion and an aperture that extends through the tubular portion; and
the aperture is rotationally aligned with the second lock apparatus when the actuator is in the second position.

8. An inserter apparatus as claimed in claim 1, wherein
the main body defines an exterior; and
the actuator is on the exterior of the main body.

9. An inserter apparatus as claimed in claim 1, wherein
the main body includes an annular groove; and
the actuator includes an annular protrusion located in the annular groove.

10. An inserter apparatus as claimed in claim 1, wherein
the actuator is configured to be secured to a medicament cartridge.

11. An inserter apparatus as claimed in claim 1, further comprising:
a third lock apparatus having a locked state configured to secure the inserter apparatus to a medicament cartridge and an unlocked state;
wherein the first trocar assembly member drives the third lock apparatus from the locked state to the unlocked state when the first trocar assembly member reaches the fired position.

12. An inserter apparatus as claimed in claim 1, wherein
at least one of the first and second force members comprises a resilient member.

13. An inserter apparatus as claimed in claim 12, wherein
the resilient member comprises a compressed spring.

14. An inserter apparatus, comprising:
a main body defining a proximal end, a distal end and a longitudinal axis;
a trocar assembly, located at least partially within the main body and movable relative to the main body, including
a first trocar assembly member movable relative to the main body in a first direction from a storage position to a fired position,
a second trocar assembly member operably connected to the first trocar assembly member such that the second trocar assembly member is movable with the first trocar assembly member in the first direction from the storage position to the fired position and the second trocar assembly member is also movable relative to the first trocar assembly member in a second direction, opposite the first direction, from the fired position to a withdrawn position,
a first spring, operably connected to the first and second trocar assembly members, that is maintained in a compressed state as the first and second trocar assemblies move from the storage position to the fired position,
a first lock apparatus having a locked state that prevents movement of the first and second trocar assembly members relative to one another and an unlocked state that permits movement of the first and second trocar assembly members relative to one another, and
a trocar carried by the second trocar assembly member;
a second spring, operably connected to the main body and to the trocar assembly, that applies a force in the first direction to the first trocar assembly member;
a second lock apparatus having a locked state that prevents movement of the trocar assembly relative to the main body relative and an unlocked state that permits movement of the trocar assembly relative to the main body; and
an actuator carried by the main body and rotatable about the longitudinal axis relative to the main body from a first position, that prevents the second lock apparatus from being in the unlocked state, to a second position that allows the second lock apparatus to be in the unlocked state.

15. An inserter apparatus as claimed in claim 14, wherein
the second spring drives the second lock apparatus from the locked state to the unlocked state, and drives the trocar assembly from the storage position to the fired position, when the actuator is in the second position.

16. An inserter apparatus as claimed in claim 15, wherein
the first lock apparatus is in the locked state when the trocar assembly is in the storage position;
the first lock apparatus transitions from the locked state to the unlocked state in response to the trocar assembly reaching the fired position; and
the first spring drives the second trocar assembly member to the withdrawn position when the first lock apparatus transitions from the locked state to the unlocked state.

17. An inserter apparatus as claimed in claim 16, wherein
the main body includes a locking surface that prevents the first lock apparatus from being in the unlocked state when the first lock apparatus is longitudinally aligned with the locking surface;
the first lock apparatus is longitudinally aligned with the locking surface when the trocar assembly is in the storage position; and
the first lock apparatus is not longitudinally aligned with the locking surface when the trocar assembly is in the fired position.

18. An inserter apparatus as claimed in claim 15, wherein
the second spring defines first and second longitudinal ends;
the first longitudinal end of the second spring engages the main body;
the second longitudinal end of the second spring engages the first trocar assembly member; and
the second longitudinal end of the second spring does not engage the second trocar assembly member.

19. An inserter apparatus as claimed in claim 14, wherein
the actuator is configured to be secured to a medicament cartridge.

20. An inserter apparatus as claimed in claim 14, further comprising:
- a third lock apparatus having a locked state configured to secure the inserter apparatus to a medicament cartridge and an unlocked state;
- wherein the first trocar assembly member drives the third lock apparatus from the locked state to the unlocked state when the first trocar assembly member reaches the fired position.

* * * * *